United States Patent
Emerit et al.

(10) Patent No.: US 6,299,377 B1
(45) Date of Patent: Oct. 9, 2001

(54) LIQUID APPLICATOR FOR THE SKIN

(75) Inventors: Michel Henri Jean Emerit; Yanick André Jean Paternotte, both of Sannois (FR)

(73) Assignee: Aspir, Sannois (FR)

( * ) Notice: Subject to any disclaimer, the term of this patent is extended or adjusted under 35 U.S.C. 154(b) by 0 days.

(21) Appl. No.: 09/530,424

(22) PCT Filed: Oct. 29, 1998

(86) PCT No.: PCT/FR98/02321

§ 371 Date: Jul. 12, 2000

§ 102(e) Date: Jul. 12, 2000

(87) PCT Pub. No.: WO99/22801

PCT Pub. Date: May 14, 1999

(30) Foreign Application Priority Data

Oct. 30, 1997 (FR) .................................................. 97 13654

(51) Int. Cl.⁷ .................................................... B05C 11/00
(52) U.S. Cl. .......................... 401/266; 401/261; 401/196; 222/541.1
(58) Field of Search ..................... 401/263, 262, 401/261, 266, 132, 133, 134, 203, 204, 205, 183, 186, 283, 290, 270, 269, 268, 207, 202, 196, 23, 25, 26, 139

(56) References Cited

U.S. PATENT DOCUMENTS

| | | | |
|---|---|---|---|
| 1,262,473 | * 4/1918 | Ensley | 401/263 |
| 2,299,236 | * 10/1942 | Hollenbeck et al. | 401/262 |
| 2,948,008 | * 8/1960 | Leeds et al. | 401/263 |
| 2,976,560 | * 3/1961 | Turner | 401/186 |
| 3,148,401 | 9/1964 | Gilchrist et al. | |
| 4,889,441 | * 12/1989 | Tice | 401/131 |
| 5,174,756 | * 12/1992 | Taylor | 434/11 |

FOREIGN PATENT DOCUMENTS

| | | |
|---|---|---|
| 1415759 | 1/1966 | (FR) . |
| 2020174A | 11/1979 | (GB) . |
| WO 9112197 | 8/1991 | (WO) . |
| WO 9113814 | 9/1991 | (WO) . |
| WO 9413352 | 6/1994 | (WO) . |

* cited by examiner

Primary Examiner—Gregory L. Huson
Assistant Examiner—Huyen Le

(57) ABSTRACT

A liquid applicator for the skin comprises a hydrophilic pad for applying liquid on a zone to be treated. It further comprises elements for connecting the pad to a cartridge storing the liquid. The connecting elements are adapted for mounting the pad opposite the liquid flow outlet from the cartridge. The invention is applicable to applicators of liquid disinfectant or of any other fluid active principle. The invention also concerns a first aid kit comprising an applicator and a cartridge initially separate, and a treatment device consisting of the applicator mounted on an initially sealed cartridge.

16 Claims, 4 Drawing Sheets

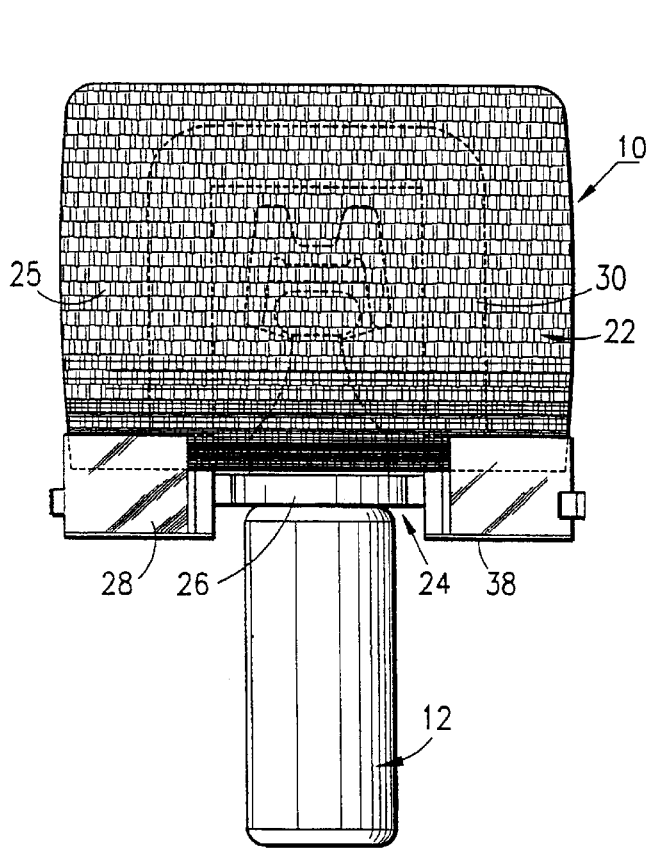
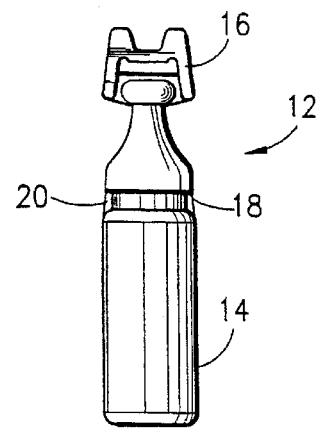
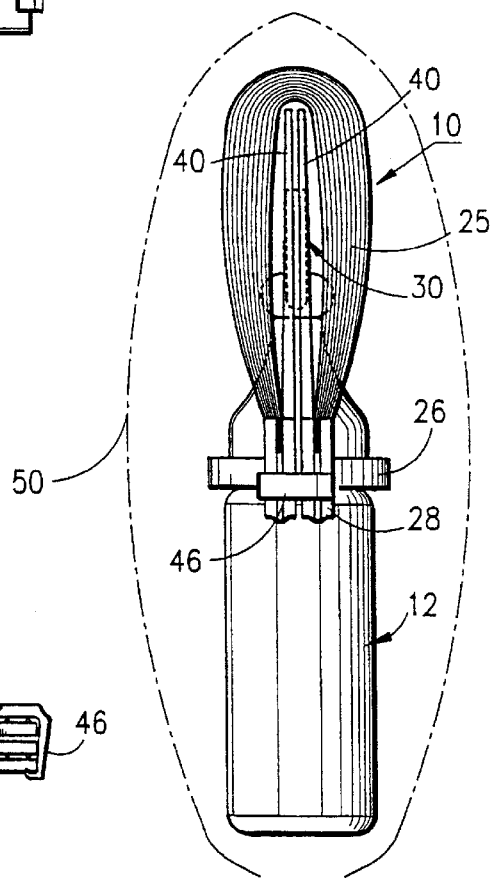
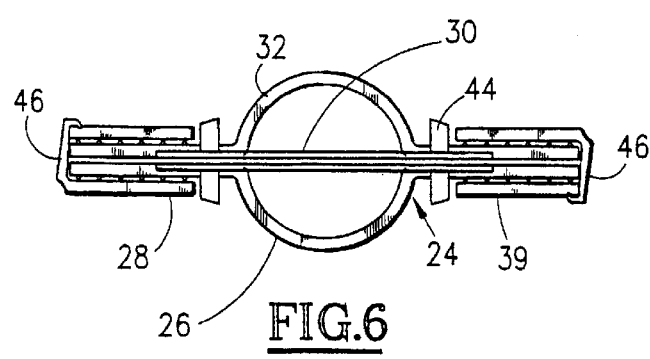

LIQUID APPLICATOR FOR THE SKIN

CROSS REFERENCE TO RELATED APPLICATION

This is the USC 35 USC 371 national stage of International application PCT/FR98/02321 filed Oct. 29, 1998, which designated the United States of America.

FIELD OF THE INVENTION

The present invention relates to an applicator for applying liquid to the skin, of the type including a hydrophilic pad for applying the liquid to the area to be treated and means for connecting the pad to a liquid storage cartridge, which connecting means are adapted for mounting the pad opposite the outlet through which the liquid flows out of the cartridge.

BACKGROUND OF THE INVENTION

It is standard practice to use a hydrophilic pad to apply a disinfectant liquid or a medication to a wound.

It is known in the art to store the hydrophilic pad and the liquid for impregnating the pad separately to prevent the hydrophilic pad drying out too quickly in is storage.

For example, document FR-A-2 732 585 describes packaging which has two initially separate compartments respectively containing a hydrophilic pad and a liquid active product. Before the pad is used, communication is established between the two compartments and the liquid active product therefore impregnates the pad.

In this type of packaging, all of the packaging must be sterile to conserve the active properties of the liquid contained in one of the compartments. Moreover, for packaging of this kind to be offered for sale, it is necessary to obtain certification which guarantees that the packaging is sterile and safe. Such certification must be obtained for each different type of packaging, which can vary in shape or volume in particular. Thus obtaining the certification is a costly and time-consuming operation which considerably increases the unit cost of the product.

Documents WO-91/12197, WO-94/13352, FR-A-1 415 759 and GB-A-2 020 174 and U.S. pat. No. 3,148,401 describe liquid applicators of the aforementioned type. However, in those applicators, the hydrophilic pad for applying the liquid is formed by a block of hydrophilic foam with a small surface area, making it difficult to apply the liquid over a large area.

SUMMARY OF THE INVENTION

The object of the invention is to propose a device for applying liquid to the skin which is adapted to receive a separately packaged liquid active product, requires no specific certification to be obtained for the applicator associated with the independently certificated container in which the liquid is stored, and enables convenient application of the liquid to a wound.

To this end, the invention provides an applicator for applying a liquid to the skin of the aforementioned type characterized in that the pad comprises a hydrophilic strip folded on itself and the connecting means include means for holding the outlet of the cartridge between the two folded edges of the strip.

In particular embodiments of the invention the applicator has one or more of the following features:

the connecting means include a collar adapted to be fixed to the neck of a cartridge;

the fixing collar includes two identical flanges fastened together and each delimiting a half-collar;

the two flanges are welded, riveted or crimped together or fixed together by at least one connecting lug in one piece with one flange and bent over the other flange;

the connecting means include means for spreading the edges of the hydrophilic strip in the area of connection to the cartridge;

each flange is extended on either side of the outlet of the cartridge by claws for retaining the ends of the hydrophilic strip;

the pad includes a flexible support to which a hydrophilic strip is fixed and the flexible support is attached to the connecting means;

the flexible support is in the general form of a hoop delimiting a housing to receive the outlet of the cartridge and possibly a stopper for closing off the latter;

the thickness of the flexible support decreases progressively from the connecting means to its end remote from the connecting means;

the connecting means allow relative movement between the applicator and the cartridge to enable a stopper blocking the outlet of the cartridge to be broken off;

it includes a member for perforating an end face of the cartridge which is adapted to be perforated;

the connecting means include a screwthread adapted to co-operate with a complementary screwthread on the cartridge to bring about said relative movement between the applicator and the cartridge;

said relative movement between the applicator and the cartridge is a rotational movement; and the applicator is packaged in a protective sachet.

The invention also provides a therapeutic kit characterized in that it includes at least one hermetically sealed cartridge containing a sterile treatment liquid and at least one applicator as defined hereinabove adapted to be mounted on a cartridge which is initially separate from the applicator.

The invention further provides a therapeutic device characterized in that it includes an applicator as defined hereinabove and a hermetically sealed cartridge containing a sterile treatment liquid and on which said applicator is mounted.

BRIEF DESCRIPTION OF THE DRAWINGS

The invention will be better understood after reading the following description, which is given by way of example only and with reference to the accompanying drawings, in which:

FIGS. 1 and 2 are respectively front and side elevation views of a therapeutic device including an applicator according to the invention mounted on a cartridge;

FIG. 3 is an elevation view of a single-use cartridge adapted to receive an applicator according to the invention;

FIG. 6 is a bottom view of the structure of the applicator support shown without the hydrophilic strip;

DETAILED DESCRIPTION OF THE INVENTION

Figure 4:
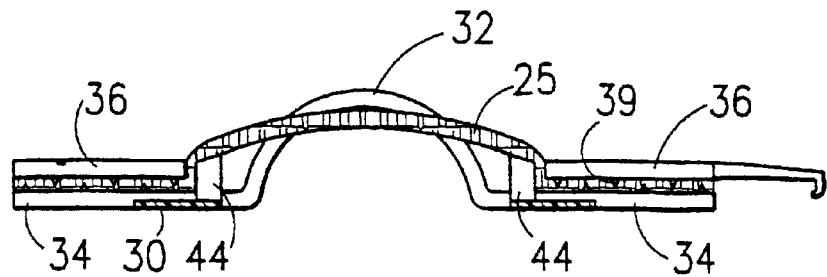
FIG. 4 is a sectional view in a median transverse plane of a blank carrying a hydrophilic strip used to form the applicator.

FIGS. 1 and 2 show an applicator 10 for applying liquid to the skin mounted on a cartridge 12 for storing a sterile liquid active product such as disinfectant or medication. FIG. 3 shows the cartridge in isolation.

Such cartridges are well known in the art and are widely used. They incorporate a substantially cylindrical flexible body 14 moulded from a plastics material, for example. The top of the body is extended by a stopper 16 moulded in one piece with the body.

Near the stopper 16 the body 14 generally has a peripheral groove 18 across which there may extend a web of plastics material 20 produced on assembling two half-shells forming the cartridge. The cartridge has a section of progressively reducing size forming a neck between the stopper 16 and the groove 18.

The capacity of such cartridges is intended to contain the quantity of liquid required for a single use. It is from 1 ml to 5 ml, for example 2.5 ml, although these values are not to be considered as limiting on the invention.

The applicator 10 shown in FIG. 1 essentially comprises a hydrophilic pad 22 and means 24 for connecting the pad 22 to the storage cartridge 12 opposite all outlet through which the liquid flows out of the cartridge. The hydrophilic pad 22 includes a hydrophilic strip 25, for example a strip of gauze.

The connecting means 24 include two identical blanks in contact with each other. They are made of polymer, for example polypropylene or polyethylene. When assembled together, they form a collar 26 for mounting on the cartridge, retaining means 28 for retaining the hydrophilic strip 25 and a hoop 30 for supporting the hydrophilic strip.

Figure 5:
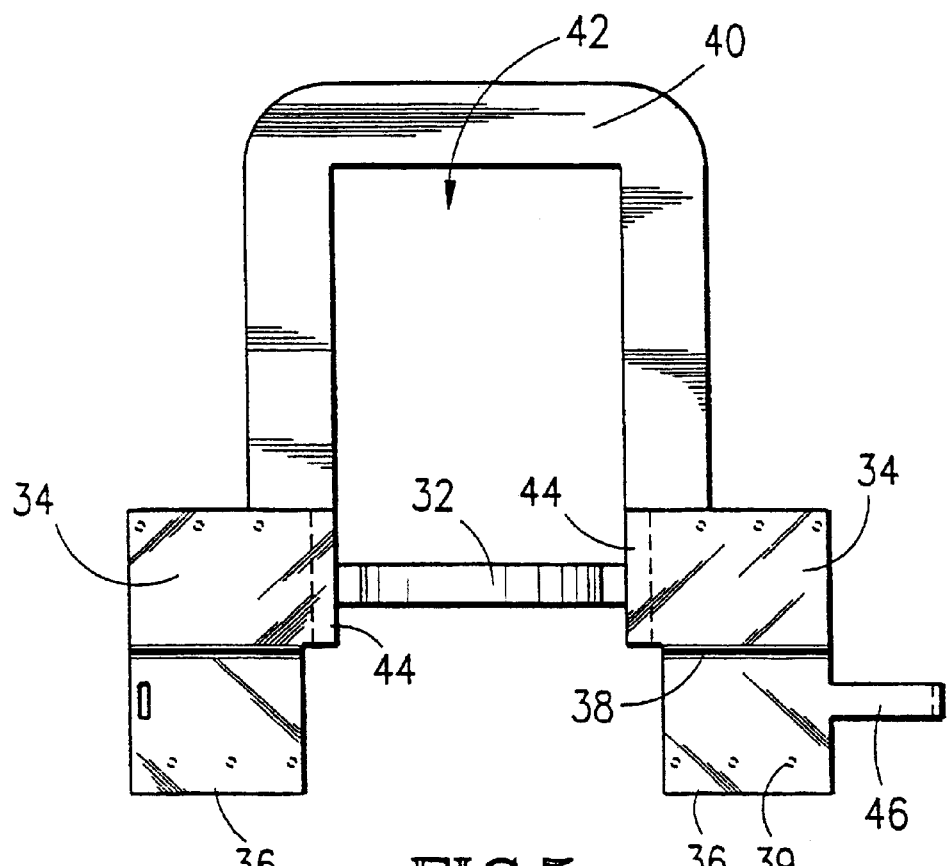
FIG. 5 is an elevation view of an applicator blank before fitting the hydrophilic strip.

FIGS. 4 and 5 show one of the blanks before the two blanks are assembled together, Each blank includes a half-collar 32 which is substantially semicircular and whose height is slightly less than the width of the groove 18. The half-collar is extended at each end by two rectangular coplanar flats 34. The lower part of each flat 34 is associated with a flap 36 moulded in one piece with and joined to the flat 34 at a bending line 38. The facing surfaces of the flats 34 and the flaps 36 carry pips 39 arranged in conjugate patterns. The pips are adapted to retain the hydrophilic strip 25. Thus the flats 34 over which the flaps 36 are bent form claws for retaining the strip 25, as shown in FIG. 4.

The top parts of the two flats 34 are joined together by a generally U-shaped arch 40 moulded in one piece with them. With the half-collar 32, the arch delimits a rectangular space 42 large enough to receive the neck of the cartridge and its stopper 16.

As shown in FIG. 2, the thickness of the arch 40 decreases progressively from the flats 34 to a transverse bridge at the end joining the two legs of the arch.

Also, the flats 34 preferably incorporate attached lateral upstands 44 on respective opposite sides of the half-collar 32 and projecting from the same side of the flats 34 and the arch 40 as the half-collar 32.

Finally, one of the flaps 36 has a curved connecting lug 46 on one outside lateral wall whose length is substantially three times the thickness of the flats 34.

The applicator is assembled as follows from two identical blanks of the kind shown in FIGS. 4 and 5 and a hydrophilic strip 25. The two blanks are fitted together around the neck of a sealed cartridge 12 so that the arches 40 and the flats 34 are superposed in pairs, with the two half-collars 32 delimiting the collar 26 received in the groove 18 on the cartridge. The hydrophilic strip 25 is then folded over both sides of the hoop 30 formed by the coupled arches 40. The length of the strip 25 is chosen so that its folded ends come into contact with the pips 39 on the flats 34 but remain at a distance from the bending lines 38. The hydrophilic strip 25 therefore has folded edges on respective opposite sides of the hoop 30 which form two opposed areas for application of the liquid product.

With the hydrophilic strip positioned in this way, the four flaps 36 are bent over the ends of the hydrophilic strip 25 about the bending lines 38.

The lugs 46 are then bent around both sides of the two blanks so that the curved ends of the lugs 46 bear on the rear face of the flaps of the opposite blank. The flaps therefore retain the hydrophilic strip and the lugs 46 fasten the two blanks together and attach the applicator to the cartridge.

The applicator 10 is retained axially on the cartridge by the collar 26 engaged in the groove 18. The collar allows the applicator to turn about the axis of the cartridge, however.

The two half-collars 32 are joined together by a crimped area of progressively decreasing width adapted to receive the web 20.

The applicator is mounted on the cartridge and they are packaged in packaging such as a transparent plastics material sachet 50, as shown in FIG. 2, under the required sterile conditions. The sterile conditions for the sachet 50 are less severe than those for the cartridge 12, since the sachet does not directly contain an active substance.

With the body of the cartridge held between the fingers, through the sachet or other packaging, rotating the applicator 10 about the axis of the cartridge 12 by pressing on the flats 34 with the fingers shears the stopper and opens the cartridge. The liquid contained in it is then free to flow out and impregnate the hydrophilic strip, in particular if manual pressure is applied to the flexible body of the cartridge.

With the pad impregnated in this way, the user can remove it from its packaging and dab the area to be treated with the pad, holding only the body of the cartridge. The liquid product is applied through contact of the area to be treated with one or other of the opposite folded edges of the strip which form the exposed areas for application of the liquid.

An applicator can also be sold separately from a cartridge with which it must be associated in use.

It is then packaged on its own in appropriate packaging. The applicator is manufactured as previously described, except for the first step, in which the two blanks are fitted together with no cartridge between them.

The applicator formed in this way can be fitted subsequently to a cartridge as shown in FIGS. 1 and 2. The upstands 44 spread the ends of the strip 25 apart in the area of the collar 26, as shown in FIG. 4. The ends of the strip, when spread apart in this way, delimit a passage into which the stopper 16 of a cartridge can be inserted The cartridge is inserted into the applicator by elastic deformation of the neck of the cartridge and the collar 26.

The stopper 16 blocking the fluid outlet is received in the rectangular space 42 delimited by the hoop 30, as shown in FIGS. 1 and 2.

The outlet of the cartridge is then inserted between the two folded edges of the strip 25.

The applicator can also be sold in the form of a therapeutic kit including one or more applicators associated with a corresponding number of sealed cartridges, the cartridges initially being separate from the applicators.

The cartridges to which the applicator in accordance with the invention is fitted are on widespread sale and have been certificated to guarantee that they are safe and sterile. Also, using off-the-shelf cartridges like these with an applicator provides a therapeutic device meeting the conditions of hygiene needed for satisfactory use. What is more, the therapeutic device does not require new certification to authorize its distribution.

Because the hoop 30 becomes progressively thinner towards its end remote from the cartridge, the pad is more flexible at the end which is intended to come into contact with the skin than at the end fixed to the cartridge, which facilitates application.

What is more, confining the ends of the hydrophilic strip between the flats 34 and the flaps 36 joined together at the bending lines 38 ensures that excess liquid is channelled into the hydrophilic strip, rather than getting onto the cartridge or the user's fingers.

In the example described, the blanks have a structure which retains the hydrophilic strip very well. They can have a simpler structure, however, for example with no flaps. The hydrophilic strip is then gripped directly between the flats 34 or fixed directly to them.

Similarly, the blanks can be welded, riveted or crimped together or fastened together by any other means, instead of by the lugs 46. The two flats can also be moulded in one piece with the hoop, in particular its upper part.

Figure 7:
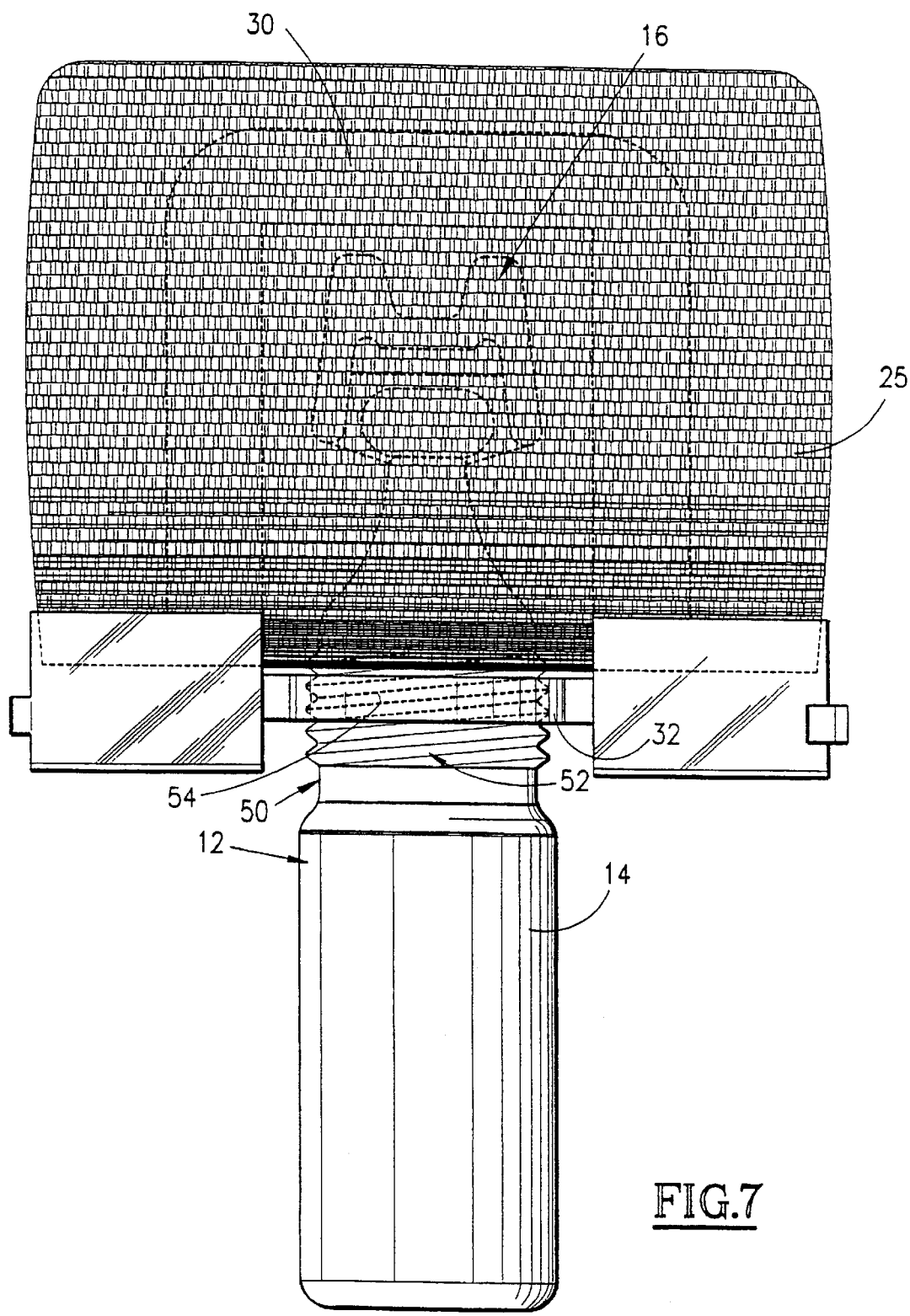
FIG. 7 is a front elevation view of a different embodiment of a therapeutic device including an applicator according to the invention.
Figure 8:
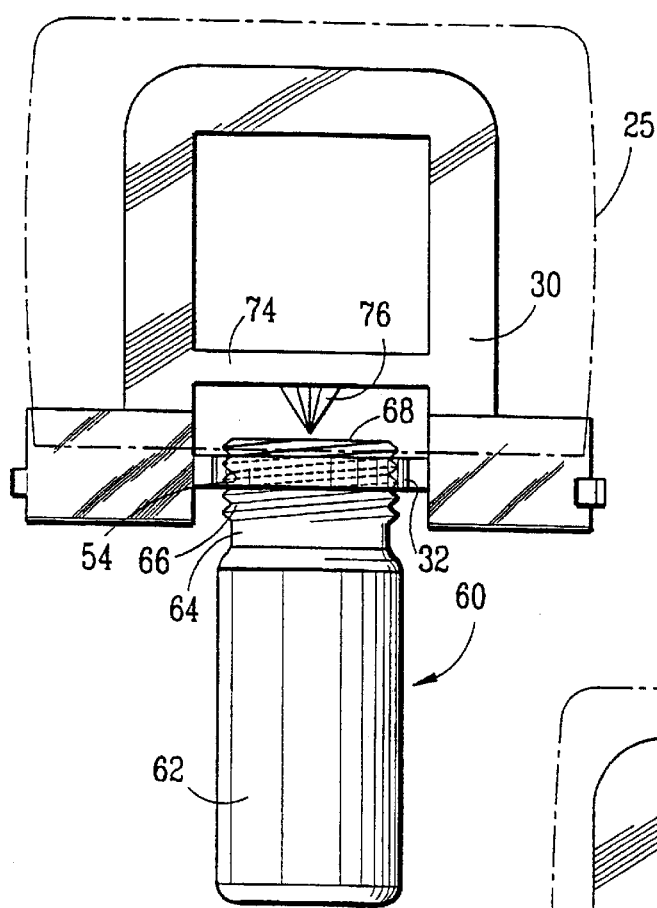
FIG. 8 is a cutaway perspective view of another embodiment of a therapeutic device.
Figure 9:
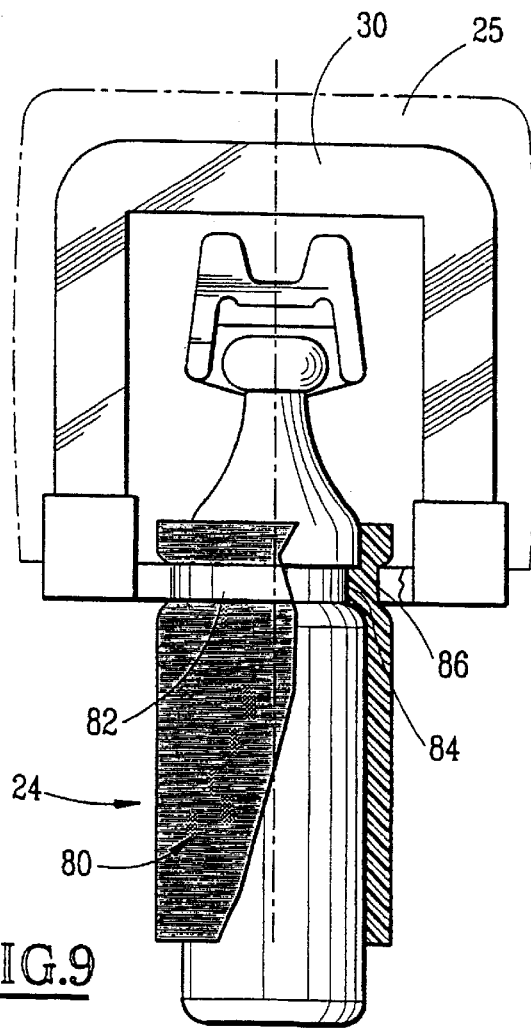
FIG. 9 is a perspective view of a further embodiment of a therapeutic device

In the embodiments of the invention shown in FIGS. 7 to 9 parts identical or analogous to those of the preceding embodiment are designated by the same reference numbers.

In the embodiment shown in FIG. 7 the storage cartridge 12 has in the region connecting the body 14 to the neck a cylindrical section 50 with an external screwthread 52 formed by a helicoidal thread moulded in one piece with the cartridge.

The semicircular section of each half-collar 32 has an internal helicoidal rib 54 forming a screwthread adapted to co-operate with the complementary screwthread 52 on the cartridge 12.

In this embodiment, as previously, the outlet through which the liquid flows out of the cartridge is initially blocked by a stopper 16 moulded in one piece with the body. The stopper 16 can be sheared off.

The applicator is initially engaged with the free end of the screwthread 52. The stopper 16 is then inside the hoop 30, between the two folded edges of the hydrophilic strip 25.

To impregnate the hydrophilic strip 25, in order no apply the liquid contained in the cartridge 12 to the area to be treated, the user screws the applicator onto the cartridge 12. This moves the applicator 10 and the cartridge 12 axially towards each other. The helicoidal movement of the applicator relative to the cartridge 12 resulting from such screwing shears off the stopper 16, which is held between the operator's fingers. This opens the cartridge. The liquid contained in the cartridge is therefore free to flow out onto the hydrophilic strip 25.

In the embodiment shown in FIG. 8 the cartridge 60 has a body 62 and a neck 64 with an external screwthread 66. The neck 64 is blocked by an end face 68 which is adapted to be perforated.

In this embodiment, the means 24 connecting the hydrophilic strip 25 to the cartridge 62 are analogous to those of the embodiment shown in FIG. 7. There is therefore a helicoidal rib 52 on the inside of each halt collar 32 adapted to co-operate with the screwthread 66.

The hoop 30 carries a crosspiece 74 extending diametrally relative to the cartridge 60. The crosspiece 74 has a perforator member 76 in the middle oriented towards the face 68 of the cartridge which is adapted to be perforated. The perforator member 76 extends along the axis of the screwthread 66.

The perforator member 76 is a ribbed spike, i.e. a generally conical member with ribs extending along its generatrices and converging at the apex of the cone.

With an arrangement like this, when the applicator is screwed onto the neck 66, the perforator member 76 stresses the face 68 which is adapted to be perforated and perforates it by progressively forcing in the perforator member 76 with its ribbed surface. Once the member 76 has been at least partly forced into the face 68, the liquid contained in the cartridge 62 is free to flow in the passages defined between the convergent ribs on the member 76. The liquid then flows between the two folded edges of the hydrophilic strip 25 and impregnates it, enabling the liquid to be applied to the area to be treated.

The applicator shown in FIG. 9 is adapted to be fitted to a cartridge 12 of the type shown in FIG. 3.

In this embodiment, the connecting means 24 include an elastic sleeve 80 around the axis of which the hydrophilic strip 25 can rotate on a ring 82 carrying the support hoop 30.

The sleeve 80 is made from an elastically deformable material. Its inside diameter is slightly less than the outside diameter of the body 14 of the cartridge. Its inside wall carries a peripheral bead 84 adapted to be received in the groove 20 on the cartridge.

The outside face of the sleeve 80 bas a groove 86 at its upper end in which the ring 82 is mounted to rotate about the common axis of the sleeve 80 and the cartridge 14. The ring 82 is made from a rigid material. It carries the hoop 30 in a diametral plane.

With an arrangement like this, the elastic sleeve 80 is forcibly fitted around the body of the cartridge 14 until the peripheral protrusion 94 is received into the peripheral groove 80. In this position the stopper 16 of the cartridge is surrounded by the hoop 30 and between the two folded edges of the hydrophilic strip 25. To open the cartridge 12, the operator turns the hydrophilic strip 25 and the stopper 16 relative to the body 14 of the cartridge. The stopper 16 is sheared off, releasing the liquid contained in the cartridge.

In all the embodiments described here the areas in which the liquid is applied to the area to be treated are formed by the exposed faces of the folded edges of the hydrophilic strip 25. These areas are large because they consist of virtually all of the exposed surface of the strip. It is therefore easy to apply the liquid to a large area to be treated, as most of the surface of the hydrophilic strip can be used to apply the active liquid.

What is claimed is:

1. An applicator for applying liquid to a skin, which comprises:
    a hydrophilic pad for applying liquid to an area to be treated;
    said hydrophilic pad comprising a hydrophilic strip folded on itself;
    connecting means for connecting the pad to a cartridge for storing the liquid;
    said connecting means being structured and arranged such that the pad can be mounted opposite an outlet through which the liquid flows out of the cartridge;

said connecting means including retaining means for retaining the outlet of the cartridge between folded edges of the hydrophilic strip; and said connecting means allowing relative movement between the applicator and the cartridge to enable a stopper blocking the outlet of the cartridge to be broken off.

2. The applicator according to claim 1, wherein the connecting means include a collar adapted to be fixed on a neck of the cartridge.

3. The applicator according to claim 2, wherein the collar includes two identical flanges fastened together and each delimiting a half-collar.

4. The applicator according to claim 3, wherein the two flanges are welded, riveted or crimped together, or fixed together by at least one connecting lug in one piece with one flange and bent over the other flange.

5. The applicator according to claim 3, wherein each flange is extended on either side of the outlet of the cartridge by claws for retaining the ends of the hydrophilic strip.

6. The applicator according to claim 1, wherein the connecting means include means for spreading the edges of the hydrophilic strip in the area of connection to the cartridge.

7. The applicator according to claim 1, wherein the hydrophilic pad includes a flexible support to which the hydrophilic strip is fixed, said flexible support being attached to the connecting means.

8. The applicator according to claim 7, wherein the flexible support is in the general form of a hoop delimiting a housing to receive the outlet of the cartridge and the stopper.

9. The applicator according to claim 7, wherein the flexible support has a thickness which decreases progressively from the connecting means to its end remote from the connecting means.

10. The applicator according to claim 1, further comprising a perforating member for perforating an end face of the cartridge which is adapted to be perforated.

11. The applicator according to claim 1, wherein the connecting means include a screwthread adapted to co-operate with a complementary screwthread on the cartridge to bring about said relative movement between the applicator and the cartridge.

12. The applicator according to claim 1, wherein said relative movement between the applicator and the cartridge is a rotational movement.

13. The applicator according to claim 1, wherein the applicator is packaged in a protective sachet.

14. The applicator according to claim 1, wherein the hydrophilic strip defines two opposite areas for applying the liquid.

15. Therapeutic kit comprising at least one hermetically sealed cartridge containing a sterile treatment liquid and at least one applicator according to claim 1 adapted to be mounted on the cartridge which is initially separate from the applicator.

16. Therapeutic device comprising an applicator according to claim 1, and a hermetically sealed cartridge containing a sterile liquid and on which said applicator is mounted.

* * * * *